(12) United States Patent
Dubuffet et al.

(10) Patent No.: US 7,157,485 B2
(45) Date of Patent: Jan. 2, 2007

(54) METHOD FOR SYNTHESIZING DERIVATIVES OF (2S,3AS,7AS)-1-[(S)-ALANYL]-OCTAHYDRO,-1H-INDOLE-2-CARBOXYLIC ACID AND THE USE THEREOF FOR PERINDOPRIL SYNTHESIS

(75) Inventors: Thierry Dubuffet, Autretot (FR); Pascal Langlois, Saint Jean de la Neuville (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 6 days.

(21) Appl. No.: 10/547,132

(22) PCT Filed: Feb. 27, 2004

(86) PCT No.: PCT/FR2004/000445

§ 371 (c)(1),
(2), (4) Date: Aug. 24, 2005

(87) PCT Pub. No.: WO2004/078708

PCT Pub. Date: Sep. 16, 2004

(65) Prior Publication Data

US 2006/0149082 A1    Jul. 6, 2006

(30) Foreign Application Priority Data

Feb. 28, 2003 (EP) ................... 03290486

(51) Int. Cl.
*A61K 31/403* (2006.01)
*C07D 209/12* (2006.01)

(52) U.S. Cl. ..................... 514/412; 548/452
(58) Field of Classification Search ......... 548/452; 514/412
See application file for complete search history.

(56) References Cited

U.S. PATENT DOCUMENTS 4,933,361 A    6/1990 Holger et al.

2006/0149082 A1*    7/2006 Dubuffet et al. ........... 548/492

FOREIGN PATENT DOCUMENTS

WO    WO 0158868    8/2001
WO    WO 03016336    2/2003

OTHER PUBLICATIONS

M Vincent, et al. "Stereoselective Synthesis of a New Perhydroindole Derivative of Chiral Iminodiacid, a Potent Inhibitor of Agiotensin Converting Enzyme", TETRAHEDRON, vol. 23, No. 16, p. 1677-1680, 1982.
International Search Report: PCT FR2004 000445, Aug. 6, 2004.
International Preliminary Examination Report: PCT 2004 000445, Aug. 31, 2004.
International Preliminary Report on Patentability: PCT/FR2004/000445—Sep. 29, 2005.

* cited by examiner

*Primary Examiner*—Golam M. M. Shameem
*Assistant Examiner*—Michael P. Barker
(74) *Attorney, Agent, or Firm*—Hueschen and Sage

(57) ABSTRACT

Process for the synthesis of compounds of formula (I):

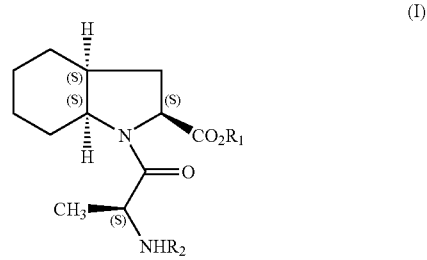

wherein $R_1$ represents hydrogen, alkyl or benzyl and $R_2$ represents a protecting group for the amine function.

Application in the synthesis of perindopril and pharmaceutically acceptable salts thereof.

6 Claims, No Drawings

US 7,157,485 B2

METHOD FOR SYNTHESIZING DERIVATIVES OF (2S,3AS,7AS)-1-[(S)-ALANYL]-OCTAHYDRO,-1H-INDOLE-2-CARBOXYLIC ACID AND THE USE THEREOF FOR PERINDOPRIL SYNTHESIS

The present invention relates to a process for the synthesis of compounds of formula (I):

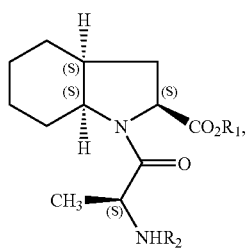
(I)

wherein $R_1$ represents a hydrogen atom or a linear or branched ($C_1$–$C_6$)alkyl or benzyl group and $R_2$ represents a protecting group for the amino function, and to their application in the synthesis of perindopril of formula (II):

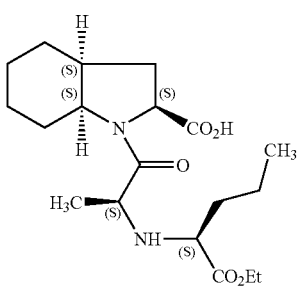
(II)

and pharmaceutically acceptable salts thereof.

Perindopril and pharmaceutically acceptable salts thereof, more especially its tert-butylamine salt, have valuable pharmacological properties.

Their principal property is that of inhibiting angiotensin I converting enzyme (or kininase II), which prevents, on the one hand, conversion of the decapeptide angiotensin I to the octapeptide angiotensin II (a vasoconstrictor) and, on the other hand, degradation of bradykinin (a vasodilator) to an inactive peptide.

Those two actions contribute to the beneficial effects of perindopril in cardiovascular diseases, more especially in arterial hypertension and heart failure.

Perindopril, its preparation and its use in therapeutics have been described in the European Patent specification EP 0 049 658.

In view of the pharmaceutical value of this compound, it has been important to obtain it by an effective synthesis process that results in perindopril in a good yield and with excellent purity, starting from reasonably priced and readily accessible starting materials.

The Patent Application EP 1 256 590 has already described a process for the preparation of compounds of formula (I).

However, that process has the disadvantage of using as starting material a (2S)-dihydroindole-2-carboxylic acid ester which is not commercially available and the preparation of which requires several synthesis steps (including a resolution step) starting from indole-2-carboxylic acid.

The Applicant has now developed a new process for the synthesis of compounds of formula (I) which has the advantage of using, as sole sources of chirality, alanine (a natural and, therefore, inexpensive starting material) and a compound readily accessible from serine.

More specifically, the present invention relates to a process for the industrial synthesis of the compound of formula (I):

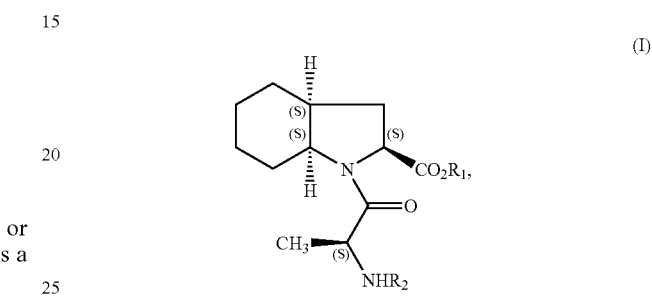
(I)

wherein $R_1$ represents a hydrogen atom or a linear or branched ($C_1$–$C_6$)alkyl or benzyl group and $R_2$ represents a protecting group for the amine function, characterised in that 1-(1-cyclohexen-1-yl)-pyrrolidine of formula (III):

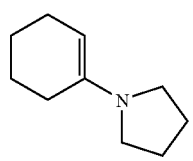
(III)

is reacted with the serine compound of formula (IV):

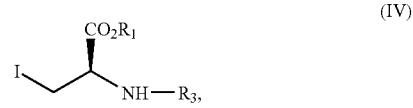
(IV)

wherein $R_1$ is as defined for formula (I) and $R_3$ represents a protecting group for the amine function, to yield the compound of formula (V):

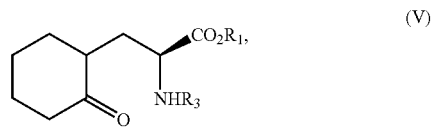
(V)

wherein $R_1$ and $R_3$ are as defined hereinbefore, the amine function of which is deprotected before cyclisation is carried out, followed by dehydration, to yield the compound of formula (VI):

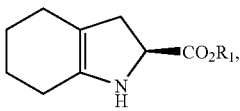

(VI)

wherein $R_1$ is as defined hereinbefore, which is reacted with the alanine compound of formula (VII):

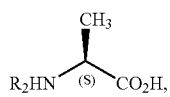

(VII)

wherein $R_2$ is as defined for formula (I), in an organic solvent such as, for example, tetrahydrofuran or ethyl acetate, in the presence of an amount of dicyclohexylcarbodiimide of from 1 to 1.2 mol per mol of compound of formula (V) used and an amount of triethylamine of from 1 to 1.2 mol per mol of compound of formula (V) used and optionally in the presence of 1-hydroxy-benzotriazole, at a temperature of from 20 to 50° C., to yield, after isolation and then recrystallisation, the compound of formula (VIII)

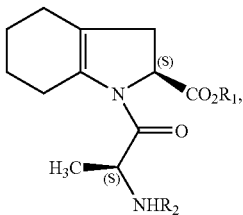

(VIII)

wherein $R_1$ and $R_2$ are as defined hereinbefore, which is hydrogenated in the presence of a catalyst such as, for example, palladium, platinum, rhodium or nickel, under a hydrogen pressure of from 1 to 30 bars, preferably from 1 to 10 bars, to yield, after optional deprotection or reprotection of the acid function, the compound of formula (I).

The compound of formula (I) obtained in that manner is then subjected, if desired, to a reaction deprotecting the acid and amine functions, followed by a coupling reaction either with ethyl 2-oxo-pentanoate under conditions of reductive amination or with a compound of formula (IX):

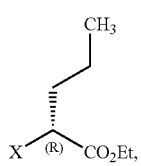

(IX)

wherein X represents a leaving group selected from a halogen atom,

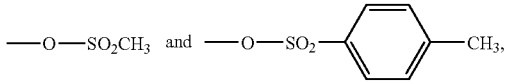

to yield optically pure perindopril, which is converted, if desired, into a pharmaceutically acceptable salt such as the tert-butylamine salt.

The compounds of formula (VIII) are new compounds which are useful as synthesis intermediates in the chemical or pharmaceutical industry, especially in the synthesis of the compound of formula (I), and as such they form an integral part of the invention.

The Example hereinbelow illustrates the invention but does not limit it in any way.

EXAMPLE (2S, 3aS, 7aS)-1-{(2S)-2 [(tert-Butoxycarbonyl)-amino]-propionyl}-octahydro-1H-indole-2-carboxylic acid Step A: Benzyl(2S)-2-[(tert-butoxycarbonyl)-amino]-3-(2-oxocyclohexyl)-propanoate Introduce 200 g of 1-(1-cyclohexen-1-yl)-pyrrolidine, 535 g of benzyl(2S)-2-[(tert-butoxycarbonyl)-amino]-3-iodopropanoate and 1.5 liters of acetonitrile into a reactor equipped with a reflux column.

Reflux for 1 hour and then return the mixture to ambient temperature. After evaporating off the solvent, add 2 liters of water and then acetic acid. Extract with ethyl acetate and evaporate to dryness.

Benzyl(2S)-2-[(tert-butoxycarbonyl)-amino]-3-(2-oxocyclohexyl)-propanoate is obtained in that manner in a yield of 80%.

Step B:
Benzyl(2S)-2-amino-3-(2-oxocyclohexyl)-propanoate

Introduce 200 g of the compound obtained in the previous Step, 1.5 liters of dichloromethane and 60 g of trifluoroacetic acid into a reactor. After stirring for 1 hour 30 minutes at ambient temperature, add 2 liters of saturated sodium hydrogen carbonate solution. Extract with dichloromethane and evaporate to dryness.

Benzyl(2S)-2-amino-3-(2-oxocyclohexyl)-propanoate is obtained in that manner in a yield of 90%.

Step C: Benzyl(2S)-2,3,4,5,6,7-hexahydro-1H-indole-2-carboxylate

In a reactor, reflux 200 g of the compound obtained in the previous Step, 13.8 g of p-toluenesulphonic acid and 1 liter of toluene, the water formed being removed by azeotropic distillation. When no more water is separated off, evaporate off the toluene.

Benzyl(2S)-2,3,4,5,6,7-hexahydro-1H-indole-2-carboxylate is obtained in that manner in a crude yield of 97%.

Step D: Benzyl(2S)-1-{(2S)-2-[(tert-butoxycarbonyl)-amino]-propionyl}-2,3,4,5,6,7-hexahydro-1H-indole-2-carboxylate With stirring, introduce 200 g of the compound obtained in the previous Step, 65 g of triethylamine and 2 liters of tetrahydrofuran into a reactor followed by, after stirring for 10 minutes at ambient temperature, 123 g of N-[tert-butoxycarbonyl]-(S)-alanine and 130 g of dicylohexylcarbodiimide. The heterogeneous mixture is then stirred at ambient temperature for 6 hours and it is then cooled to 0° C. and filtered.

The filtrate is then washed and then recrystallised from a mixture of hexane/ethyl acetate 10/1 to yield the expected product in a yield of 81% and a chemical purity of 98%.

Step E: (2S, 3aS, 7aS)-1-{(2S)-2[(tert-Butoxycarbonyl)-amino]-propionyl}-octahydro-1H-indole-2-carboxylic acid Introduce 200 g of the compound obtained in the previous Step, dissolved in acetic acid, and then 5 g of Pt/C 10% into a hydrogenator. Hydrogenate under a pressure of 5 bars at ambient temperature until the theoretical amount of hydrogen has been absorbed.

Remove the catalyst by filtration and then cool to a temperature of from 0 to 5° C. and collect the resulting solid by filtration. Wash the filter cake and dry it to constant weight. (2S, 3aS, 7aS)-1-{(2S)-2[(tert-Butoxycarbonyl)-amino]-propionyl}-octahydro-1H-indole-2-carboxylic acid is obtained in that manner in a yield of 87% and an enantiomeric purity of 99%.

The invention claimed is:

1. A process for the synthesis of compounds of formula (I):

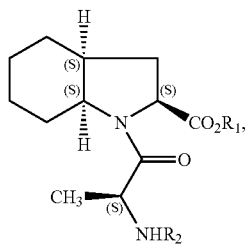

(I)

wherein $R_1$ represents hydrogen, linear or branched ($C_1$–$C_6$)alkyl or benzyl, and $R_2$ represents a protecting group, wherein 1-(1-cyclohexen-1-yl)-pyrrolidine of formula (III):

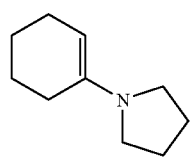

(III)

is reacted with a serine compound of formula (IV):

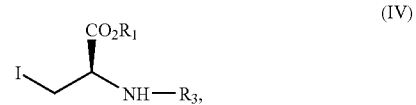

(IV)

wherein $R_1$ is as defined for formula (I) and $R_3$ represents a protecting group, to yield a compound of formula (V):

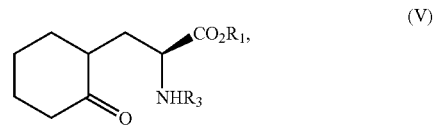

(V)

the amine function of the compound of formula (V) is deprotected and the deprotected intermidiate thus obtained is subjected to dehydration, to yield a compound of formula (VI):

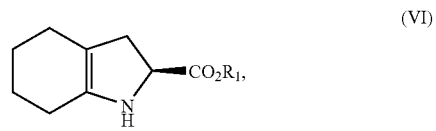

(VI)

which is reacted with an alanine compound of formula (VII):

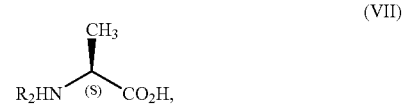

(VII)

wherein $R_2$ is as defined for formula (I), in an organic solvent, in the presence of an amount of dicyclohexylcarbodiimide of from 1 to 1.2 mol per mol of compound of formula (V) used and an amount of triethylamine of from 1 to 1.2 mol per mol of compound of formula (V) used and optionally in the presence of 1-hydroxybenzotriazole, at a temperature of from 20 to 50° C., to yield, after isolation and recrystallisation, a compound of formula (VIII):

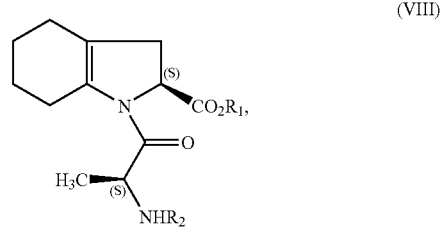

(VIII)

which is hydrogenated in the presence of a catalyst, under a hydrogen pressure of from 1 to 30 bars, to yield, after optional deprotection or reprotection of the acid function, the compound of formula (I).

2. The process of claim 1, wherein the hydrogen pressure during the hydrogenation reaction is from 1 to 10 bars.

3. The process of claim 1, wherein the catalyst is selected from palladium, platinum, rhodium and nickel.

4. The process of claim 1, wherein $R_1$ represents hydrogen and $R_2$ represents tert-butoxycarbonyl.

5. A process for the synthesis of perindopril or a pharmaceutically acceptable salt thereof, wherein the compound of formula (III) is converted into the intermediate compound of formula (I) according to the process of claim 1, and then the intermediate compound of formula (I) is converted into perindopril or a pharmaceutically acceptable salt thereof.

6. A compound of formula (VIII):

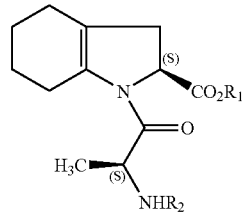

(VIII)

wherein $R_1$ represents hydrogen, linear or branched $(C_1-C_6)$alkyl or benzyl, and $R_2$ represents a protecting group.

* * * * *